United States Patent [19]

Underwood

[11] Patent Number: 4,650,792
[45] Date of Patent: Mar. 17, 1987

[54] MOSQUITO ABATEMENT

[76] Inventor: Dennis Underwood, 4154 N. Woodlawn Ave., Decatur, Ill. 62526

[21] Appl. No.: 381,391

[22] Filed: May 24, 1982

Related U.S. Application Data

[63] Continuation of Ser. No. 170,125, Jul. 18, 1980, abandoned.

[51] Int. Cl.$^4$ ............................................. A01N 57/00
[52] U.S. Cl. ..................................... 514/89; 514/102; 514/107; 514/75
[58] Field of Search ............. 424/198, 75, 200, 79.94, 424/204, 102; 514/89, 107, 102, 79

[56] References Cited

U.S. PATENT DOCUMENTS

| | | | |
|---|---|---|---|
| 3,244,586 | 4/1966 | Rigterink | 260/960 |
| 3,317,636 | 5/1967 | Lovell et al. | 424/206 |
| 3,492,405 | 1/1970 | Hamm | 424/224 |
| 3,903,289 | 9/1975 | Magee | 424/275 |
| 3,975,420 | 8/1976 | Hurt | 424/215 X |
| 4,008,319 | 2/1977 | Hurt | 424/212 X |
| 4,029,774 | 6/1977 | Hurt | 424/216 |
| 4,081,536 | 3/1978 | Nelson | 424/203 X |
| 4,112,083 | 9/1978 | Hurt | 424/215 |
| 4,357,329 | 11/1982 | Heywang et al. | 424/204 X |

FOREIGN PATENT DOCUMENTS

| | | |
|---|---|---|
| 848945 | 8/1970 | Canada . |
| 111917 | 7/1962 | Pakistan . |

OTHER PUBLICATIONS

Kirk–Othmer, 2 Ed, vol. 11, p. 731.
"Abate Insecticide in Public Health Programs—Comprehensive Research Development Manual" pp. 42–43.
Down to Earth, vol. 23, No. 2 (Fall 1967); Mulla.
The Merck Index, 8th Ed., (1968); p. 800.

Primary Examiner—Leonard Schenkman
Assistant Examiner—Joseph A. Lipovsky
Attorney, Agent, or Firm—Wood, Dalton, Phillips, Mason & Rowe

[57] ABSTRACT

A granulor formulation of a mosquito larvicide is prepared by impregnating corncob granules with an oil suspension or solution of a suitable toxicant in order to deposit the material on the surface of the granules. The impregnated granules float and are suitable for dispersion over a wide variety of larval mosquito sources.

18 Claims, 1 Drawing Figure

U.S. Patent  Mar. 17, 1987  4,650,792
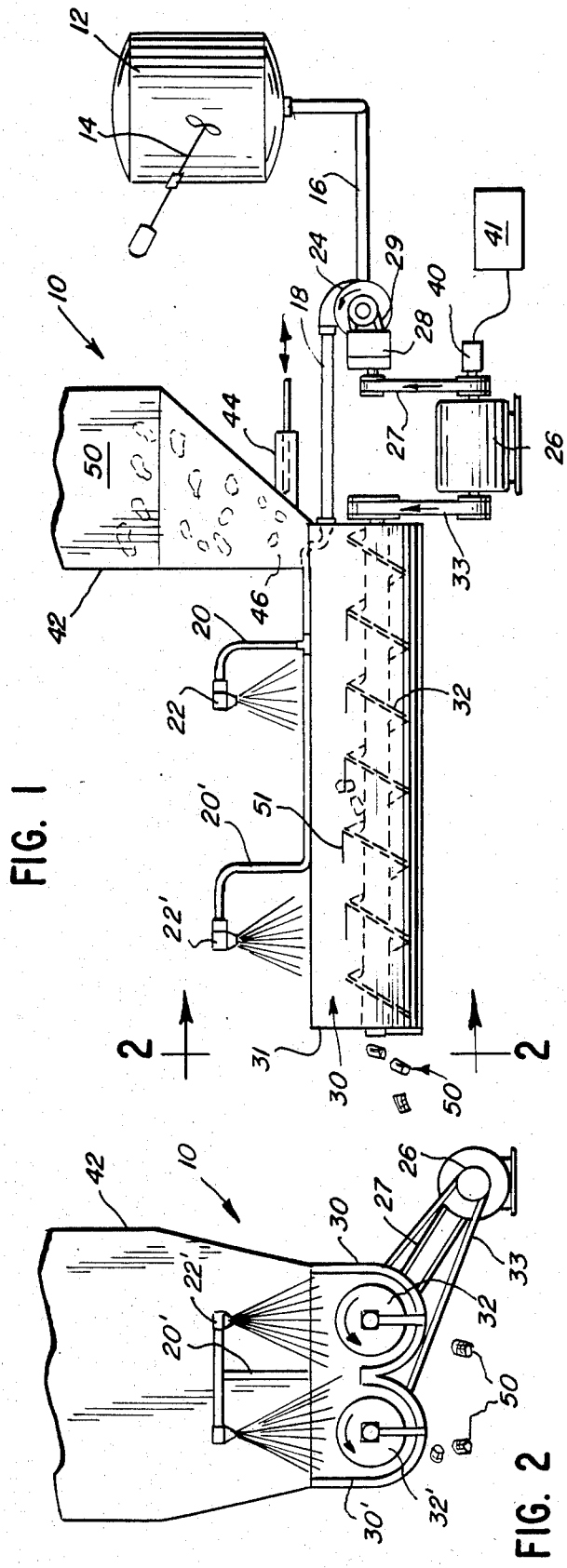
FIG. 1
FIG. 2
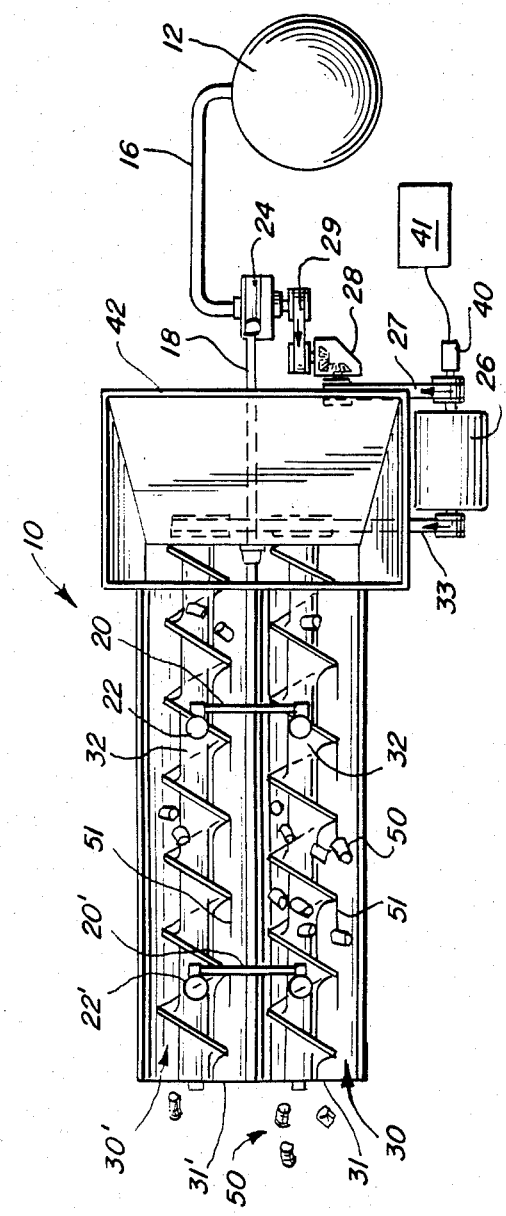
FIG. 3

MOSQUITO ABATEMENT

BACKGROUND OF THE INVENTION

This is a continuation of application Ser. No. 170,125, filed July 18, 1980, now abandoned.

1. Field of the Invention

This invention relates to mosquito abatement and, more particularly, this invention relates to a granular formulation of insecticides and a method of dispersing insecticide using the granular formulation.

2. Brief Description of the Prior Art

The use of liquid and granular insecticide formulations in mosquito abatement is well known. As used herein, the term "insecticide" is a generic term denoting toxicants useful in abatement of mosquitoes as well as other insects, both as adults (adulticides) and larvae (larvicides).

Prior liquid insecticide formulations generally comprised a liquid insecticide active ingredient dispersed in a suitable solvent system for application directly to an area in which mosquito larvae are present in order to toxify the area. Liquid larvicidal formulations are unsuitable for use on floodplains or other sources of mosquito larvae having high concentrations of floating organic matter, and are especially unsuitable for aerial application over areas beneath a foliage canopy. In such areas the canopy tends to become contaminated with insecticide, and insufficient insecticide is delivered to the underlying water surface to toxify the surface.

In order to overcome the problems associated with the use of liquid insecticide formulations in foliage-covered bodies of water, granular insecticide carriers have been utilized, the object being to penetrate overlying foliage in order to deliver the formulation to the water surface. Various solid materials have been proposed for use as insecticide carriers, including clay materials, vermiculite, or organic materials such as rice husks. However, prior solid insecticide carriers have not been entirely satisfactory, for various reasons.

Certain carrier materials, notably clay, are not buoyant in water, and hence sink to the bottom of the water upon absorbing sufficient moisture. Since toxification of a floodplain or other areas with irregular water depths is effected by delivery and maintenance of a sufficiently high insecticide concentration in a gi ven volume of water, uneconomically high quantities of prior non-buoyant granular insecticide formulations have been required in order to toxify the entire volume of floodplain areas where mosquito larvae are developing.

Other carriers such as vermiculite or rice husks, or finely ground clay are unfavorable for dispersal from aircraft because of their low density. When wind velocity exceeds 10-15 mph these materials have a greater tendency to drift following release from aircraft. This creates difficulties in the proper delivery of the insecticides to the targeted area and results in toxification of non-target peripheral zones.

This problem is complicated by the fact that mosquito larvae generally inhabit floodplain waters from the surface to a maximum depth of only about six inches. Floodplain areas capable of producing mosquito larvae have an irregular water depth varying from a few inches to about eight feet.

A further problem with prior non-buoyant carrier materials is the tendency of floodplains to be characterized by irregular currents and eddies which cause mosquito larvae to concentrate at various points on the floodplain surface. Sinkable insecticide carriers do not concentrate insecticide at such areas on the surface.

In view of the foregoing problems, the use of buoyant insecticide carriers has been proposed in order to toxify the surface and adjacent water of floodplains, and to accurately deliver insecticide to areas of larval concentrations.

Heretofore, however, no buoyant granular carrier material having acceptable insecticide release characteristics suitable for aerial dispersion has been commercially available. The use of rice husks as a carrier material has been proposed but the density of rice husks is insufficient to allow efficient aerial dispersal.

SUMMARY OF THE INVENTION

It is an object of the invention to overcome one or more of the problems described above.

According to the invention, a granular formulation of insecticide comprises a carrier of ground corn cobs which have been impregnated with a suspension or solution of a suitable insecticide such that the insecticide is deposited on the corncob surface.

The granular formulation of insecticide of the invention is suitable for aerial dispersion over river or stream floodplains whether or not the floodplain surface is covered by a foliage canopy. The formulation easily penetrates canopies of different characteristics and floats on the floodplain surface for a period of time sufficient to release the active insecticide ingredient and thereby toxify the surface and adjacent waters of the floodplain.

Furthermore, the granular formulation tends to concentrate on the surface in the same pattern as larvae, thus concentrating insecticide in the most heavily populated portions of the floodplain.

The insecticide suspending agent is preferably one in which the insecticide has only limited miscibility. The use of an insecticide suspension allows flexibility and accurate control of the amount of insecticide deposited on the carrier, thus allowing accurate regulation of the amount of insecticide dispersed over a given area.

The granular formulation of insecticide is easily prepared by means of controlled rate spray equipment which delivers insecticide to corncob granules in a controlled rate conveyor such as described below. The formulation is suitable for use with known aerial dispersion equipment.

Other objects and advantages will be apparent from the following detailed description, the drawings and the appended claims.

BRIEF DESCRIPTION OF THE DRAWINGS

FIG. 1 is a vertical section of an apparatus suitable for preparing the granular formulation of insecticide of the invention;

FIG. 2 is a vertical section of the apparatus of FIG. 1 taken generally along line 2—2 of FIG. 1; and FIG. 3 is an overhead view of the apparatus of FIGS. 1 and 2.

DETAILED DESCRIPTION OF THE INVENTION

According to the invention, a granular formulation of insecticide suitable for aerial dispersion to river or stream floodplains, including floodplains covered by a foliage canopy, comprises ground corncob granules which have been impregnated with a suspension or solution of an appropriate insecticide composition. The granules are preferably ¼"-⅜" in diameter.

The impregnated corn cobs, when deposited on the floodplain surface, float on the surface for a period of time sufficient for release of the active insecticide ingredient in order to toxify the surface and the adjacent underlying water. After about 4-6 hours, the corn cobs sink to the bottom of the floodplain.

The insecticidal suspension is preferably prepared with a suspending agent in which the insecticide has only limited miscibility. Suitable solvents for several commercially available insecticides include #1 or #2 diesel oil, mineral seal oil solvent, and a solvent marketed under the designation Odorless Solvent, Petroleum Naptha by the Ashland Chemical Company.

The granular formulation of insecticide is easily prepared. To a quantity of ground corncob granules is added, preferably by spraying, a regulated quantity of the suspension or solution. The suspending agent or solvent is readily absorbed by the corncob granules, resulting in deposition of the active insecticide ingredient on the cob surface. The formulation is suitable for storage or immediate use.

The use of insecticide in suspension or solution form allows accurate regulation of the quantity of insecticide applied to the corncob granules. This in turn allows control of the amount of active insecticide dispersed over a given floodplain area.

The use of the granular formulation of the invention results in effective insecticidal and larvicidal action from a relatively low amount of active insecticide ingredient per unit area of floodplain. Thus, the invention provides an economical, easy to use vehicle for delivery of insecticide to areas in which mosquito larvae develop.

The components of the formulation, a method of preparing the formulation, and a method of dispersing insecticide using the formulation are set forth in detail below.

THE CARRIER

Relatively dry ground corn cobs, in granular form, provide an excellent carrier for dispersion over water.

Corn cobs are widely available in great supply at low cost, and are easily ground by equipment well known in the size reduction art. Although the moisture content of cobs used in this invention is not critical, cobs having 2-3% moisture content have been used with great success.

The exact diameter of the ground corncob granules is not critical, but the general size range described as the ¼-⅜" grind is necessary for the proper functioning of the invention. This size range has been shown to exhibit optimum characteristics as to buoyancy, pattern of dispersal, and reducing susceptibility to drift when applied from aircraft.

Also, those skilled in the art will recognize that available surface area per unit weight of the granules increases with a decrease in granular diameter. However, the granule diameter should not be reduced to an extent that the cobs become powdery or have a substantial content of "fines". The granule size of ¼-⅜" has been found to provide excellent results.

Preferably, the cob granules should be sieved before impregnation with insecticide in order to remove excess fines.

THE INSECTICIDE

Any of a wide variety of water soluble and insoluble formulations of liquid larvicides or insecticides registered by the United States Environmental Protection Agency and effective against adult or larval mosquitoes or other insects may be utilized according to the invention.

Two commercially available organophosphates which are suitable for use in the invention are ABATE ® insecticide marketed by the Cyanamid International Division of American Cyanamid Company, and DURSBAN ® insecticide marketed by the Dow Chemical Company.

The active ingredient of ABATE ® insecticide is 0,0,0',0'-tetramethyl 0,0'-thiodi-p-phenylene phosphorothioate (also denoted as "temephos") and has the following structure:

$$(CH_3O)_2P(=S)-O-\phantom{x}\text{—}\phantom{x}-S-\phantom{x}\text{—}\phantom{x}-O-P(=S)(OCH_3)_2$$

ABATE ® insecticide is commercially available in both granular and liquid form. Liquid ABATE ® is available as an emulsifiable concentrate containing 200 or 500 g temephos/l, and is relatively insoluble in water and in aliphatic petroleum solvents. ABATE ® insecticide is soluble to at least a limited extent in a number of aromatic hydrocarbons.

The manufacturer's suggested usage rate of liquid ABATE ® per acre of floodplain under normal field operating conditions is 0.5-1.5 fl.oz. which corresponds to 0.016-0.048 lb/acre of active ingredient, for use against mosquito larvae.

ABATE ® insecticide is also available in granular form supported on clay mineral material. The suggested granular form usage rate suggested by the manufacturer varies between 0.05-0.5 lb. active ingredient per acre, depending on the extent of organic matter and pollution.

The active ingredient of DURSBAN ® insecticide is 0,0-diethyl 0-(3,5,6-trichloro-2-pyridyl)phosphorothioate and, according to the manufacturer, is effective in liquid form at the rate of 0.005-0.01 lb/acre in the treatment of mosquito larvae and adults. The rate required for the control of mosquitoes in log ponds is about 0.05 lb/acre.

It is emphasized that the invention is not limited to the use of a specific insecticide, but may incorporate any of a wide variety of insect control agents.

SUITABLE SUSPENDING AGENTS

In order that the surface area of the corncob granules be uniformly coated with insecticide, it is highly preferred that the insecticide be suspended in a suitable suspending agent. It should be understood, however, that acceptable results are obtainable with the use of an insecticide solution, as opposed to a suspension. Also, commercially available insecticide formulations may be applied directly to cobs without a solvent, if desired. Reference herein to the preferred "suspension" should not be construed as a limitation of the scope of the invention.

It is highly preferred that the insecticide be suspended in a liquid in which the insecticide is only moderately miscible, as the uniformity of insecticide dispersion on the cob surface has been found to be enhanced with the use of such a suspension. The suspending agent is absorbed into the interior of the cob granules, leaving a coating of insecticide active ingerdient on the surface. An emulsifier is not required and, depending on the nature of the insecticide and suspending agent, may be undesirable.

Light aromatics are generally undesirable since they are relatively highly volatile and therefore evaporate very quickly after deposition on cob granules, resulting in relatively non-uniform coating of the granules.

Information regarding the solubility of commercially available insecticides is obtainable from the respective manufacturers. In the case of the highly preferred ABATE ® insecticide, a petroleum fuel oil, such as #1 or #2 diesel oil, or a mineral seal oil, or a solvent such as marketed by the Ashland Chemical Company under the designation "Odorless Solvent, Petroleum Naptha" is highly preferred. ABATE ® insecticide has only limited miscibility in such oils.

Formulation of the insecticide suspension may be carried out conventionally by agitation on either a batch or continuous basis, with the proportions of constituents being determined, within a wide range, for convenience. The suspension may conveniently contain between about 2–5% (w/w) insecticide active ingredient.

The suspension should preferably be applied uniformly to the cob granules. Care should be taken that sufficient suspension is provided to the granules to result in uniform coating thereof, yet not so much as to result in a greasy, sticky product. The proper proportion of suspension to cobs is readily empirically determined, and specific examples are set forth below.

PREPARATION OF GRANULAR INSECTICIDE FORMULATION

FIGS. 1–3 illustrate an apparatus suitable for preparation of a granular insecticide formulation according to the invention. It is to be understood, however, that the particular apparatus used to prepare the formulation may take any of various forms; and preparation may be carried out on either a batch or a continuous basis.

An apparatus, generally designated 10, comprises a holding tank 12 having an internal agitator 14. The tank 12 is connected by conduits 16, 18, 20 and 20' to two pairs of flat fan spray nozzles 22, 22'. A constant pressure pump 24 driven by a motor 26, a belt 27, appropriate gearing 28 and a belt 29 conveys agitated insecticide suspension from the tank 12 to the nozzles 22, 22'. A convenient suspension flow rate is between about 40–45 oz/min.

The spray nozzles 22, 22' overlie and are directed downwardly onto a pair of parallel open-faced conveyor chutes 30, 30', each having an open discharge end 31, 31'. Extending through and coaxial with the chutes 30, 30' are a pair of grain auger screws 32, 32' driven by the motor 26 and a belt 33. The augers 32, 32' will generally be between about 4–9" in diameter, and may conveniently deliver between about 40–50 lb. granules/min.

A series of baffles 51, welded onto the grain auger screws 32, 32' greatly enhances the movement of the corncob granules 50, through the apparatus and cleans the auger screws of granules which may adhere to their surfaces. These also enhance the uniformity with which the insecticide suspension is applied to the corncob granules.

Density of corn cobs varies only slightly, and seed corn cobs are relatively heavy in comparison to other cobs. If cobs of widely varying density are encountered, regulation of cob flow rate may be carried out on a volume, rather than weight, basis.

Adjustment of the gearing 28 and the belts 27, 29 allows the suspension flow rate to the nozzles 22, 22' to be adjusted relative to the speed of the augers 32, 32'. An electric clutch 40 is operatively connected to the motor 26 for selective disengagement of the pump 24 from the motor 26. Means 41 are provided for controlling the speed of the motor 26.

Disposed above and communicating with one end of the chutes 30, 30' is a corncob hopper 42. The opposite end 31, 31' of each chute 30, 30' is open for discharge of material.

A horizontal metering gate 44 is disposed in a throat 46 of the hopper 42 adjacent the chutes 30, 30' for delivery of corncob granules 50 to the chutes 30, 30'. Rotation of the augers 32, 32' effects conveyance of the corncob granules at a rate controlled by the speed of the motor 26 toward the discharge end 31 of the chutes 30, 30'.

Insecticide is maintained in suspension with the suspending agent by agitation of the contents of the tank 12 by the agitator 14.

The flow rate of insecticide suspension from the nozzles 22, 22' and the rate of conveyance of corncob granules through the chutes 30, 30' are independently controllable by selection of the motor speed and pumping rate.

During travel through the chutes 30, 30', the corncob granules undergo continuous mixing and agitation such that they are uniformly sprayed with and thus impregnated with insecticide suspension sprayed from the nozzles 22, 22'.

The suspension flow rate and auger speed are regulated such that a predetermined amount of suspension is sprayed onto the corncob granules 50, to give the optimum coating and overall "wetness" before discharge thereof from the chutes 30, 30'.

It has been found that a desired granule active ingredient concentration may be obtained with as little as 3% error with the apparatus described above.

Upon discharge from the chutes 30, 30', the impregnated granules 50 may be stored, or used immediately.

METHOD OF DISPERSAL OF GRANULAR INSECTICIDE FORMULATION

While the granular formulation of the invention may be applied to river or stream floodplains, or to other areas in which mosquito larvae develop, by a variety of methods including hand distribution or distribution from terrain vehicles, dispersal is most conveniently and efficiently carried out by aircraft, typically by helicopter. One advantage of the formulation is that it does not clog aircraft-borne distributing means commonly used for this purpose.

The granular formulation of insecticide may be distributed over open water, or over floodplain areas having a foliage canopy, since the density of the granules is sufficient to effectively penetrate even heavy foliage without significant contamination thereof and without significant loss due to air movements.

After contacting the water surface, the granules float at the surface and immediately begin release of the insecticide active ingredient over the floodplain surface without substantial contamination of the water with solvent or suspending agent. The granules float at the water surface for about 4–6 hours, and then sink to the bottom of the floodplain, at which time release of insecticide is substantially complete.

In addition to toxification of the water surface, the water is fully toxified to a depth of at least 1–2 inches, where the great majority of larvae occur.

Furthermore, the granules tend to be carried over the surface by currents and eddies and to concentrate on the surface in patterns similar to those of water-borne mosquito larvae. Thus, concentrated insecticide strength is provided by the granules in those areas of the floodplain surface where it is most needed. Of course, in floodplains not characterized by currents and eddies, the granule distribution tends to be uniform over the floodplain surface, as are the target mosquito larvae.

By control of the respective flow rates of corncob granules and insecticide suspension during preparation of the formulation, the weight percentage of insecticide active ingredient in the formulation may be adjusted over a wide range. It has been found that effective insecticidal and larvicidal activity is obtained with conveniently low amounts per acre of impregnated granules having as low as 0.1–0.5% active ingredient. Generally, only 10–30 lb/acre of impregnated granules having 0.1–0.5 wt.% active ingredient need be applied. Specific examples appear below.

Effective larvicidal activity is obtained under normal field conditions by application of as low as 30 lb. impregnated granules/acre at a 0.1% active ingredient level. However, as low as 10–20 lb. impregnated cobs-/acre may be utilized at a 0.1% active ingredient level if relatively little foliage canopy and organic pollutants are encountered. An application rate of 20 lb. cob granules/acre corresponds to an average of about 1 granule/24 $in^2$.

It will be readily apparent that the use of controlled amounts of the suspending agent aids in regulation of formulation concentration, thus contributing to the predictability and dependability of the use of the formulation of the invention.

EXAMPLE

The practice of the invention is more fully illustrated with reference to the following specific example, which is not intended to be taken by way of limitation.

An apparatus such as illustrated in FIGS. 1-3 is used to prepare a granular insecticide formulation, as follows:

A 3.4% (w/w) suspension of ABATE® insecticide active ingredient in #1 diesel fuel oil is prepared by mixing at room temperature and is agitated in a tank 12. A quantity of ¼" diameter (nominal) corncob granules is charged to a hopper 42 and conveyed through a pair of open-faced chutes 30, 30' having 4" diameter augers at an overall rate of 45 lb/min.

The suspension is pumped to two pair of spray nozzles 22, 22' at an overall rate of 43 oz/min, to provide a quantity of impregnated corncob granules having an insecticide active ingredient content of about 0.2% (w/w). The product granules are substantially dry to the touch and are non-greasy and non-sticky, and do not tend to agglomerate.

Five floodplain mosquito producing sites are treated by helicopter using the foregoing formulation on two dates roughly one month apart. On the first date, third and fourth instar larvae are streated at a rate of 20 lb. granules/acre. On the second date, second instar larvae are treated at the same overall rate, but dispersal is accomplished by a "crosshatch" application pattern wherein each area is treated twice at 10 lb/acre, resulting in reduced pilot error and therefore, it is believed, improved uniformity of dispersal.

Larva populations in each area are sampled before and after treatment at several stations in each area established at points with different water depth and canopy density. Counts are made by averaging the number of larvae in 30 dips (1 pint enamel dipper) in a 25 yard radius from the central station point. Dips are biased toward points where presence of larvae is most likely.

Test results are given below in the Table.

| Site # | Acreage Treated | Instar Treated | % Kill 24 Hr. Post-Treatment | % Kill 48 Hr. Post-Treatment |
|---|---|---|---|---|
| 1 | 15 | 3rd/4th | 76% | 94% |
| | 15 | 2nd | 98% | 98% |
| 2 | 8 | 3rd | 97% | 98% |
| | 8 | 2nd | 100% | 100% |
| 3 | 12 | 3rd/4th | 50% | 98% |
| | 12 | 2nd | 90% | 95% |
| 4 | 23 | 3rd/4th | 96% | 98% |
| | 23 | 2nd | 94% | 94% |
| 5 | 25 | 3rd/4th | 90% | 94% |
| | 25 | 2nd | 100% | 100% |

In the foregoing example, a 3.4% (w/w) insecticide suspension is used. It has been found convenient to vary final granule insecticide concentration by varying the suspension insecticide concentration and maintain the cob granule and spray flow rates constant.

Convenient final insecticide active ingredient concentrations in the product granules may be of 0.1±0.003% to 0.5±0.015% depending on the final concentration desired to adapt to local conditions.

It will be appreciated that the granular formulation of insecticide and the method of application detailed above provides an effective means of delivering insecticide to the surface of mosquito development areas, at which surface-dwelling insect larvae are present and therefore most susceptible to toxification.

It will be further appreciated that effectiveness and efficiency of the formulation and method of application are totally independent of the depth of floodplain or other body of water in connection with which they are used, since delivery of insecticide is confined to the surface and adjacent water of the area, and the entire volume of water need not be toxified, as with currently marketed sinkable granular formulations.

The foregoing detailed description is given for clearness of understanding only, and no unnecessary limitations should be inferred therefrom, as modifications will be obvious to those skilled in the art.

I claim:

1. A method of preparing a granular insecticide composition especially adapted for aerial distribution over flooded or flood-prone areas through a foliage canopy, said method comprising the steps of:

(a) providing a quantity of corncob granules having nominal diameters between about ¼ inch and ⅜ inch;

(b) providing a quantity of a suspension of an insecticide in a liquid suspending agent with which said insecticide has only limited miscibility;

(c) impregnating said corncob granules with said suspension while regulating the respective quantities of said corncob granules and said suspension, and the concentration of insecticide in said suspension to provide an effective amount of said insecticide on said impregnated granules, whereby said suspending agent is absorbed into said corncob granules and an effective amount of said insecticide is deposited on the surface of said corncob granules.

2. The method of claim 1 wherein said insecticide comprises a liquid organophosphate insecticide, said suspending agent comprises a liquid hydrocarbon, and said insecticide comprises between about 2% and 5%, by weight, of said suspension.

3. The method of claim 2 wherein said liquid hydrocarbon is chosen from the group consisting of #1 diesel oil, #2 diesel oil, and petroleum naptha.

4. The method of claim 1 wherein said suspension is applied to said corncob granules by spraying during agitation of said granules to effect substantially uniform impregnation of said granules with said suspension.

5. The method of claim 1 wherein said corncob granules are prepared by grinding corn cobs.

6. The method of claim 1 wherein the respective quantities of said corncob granules and said suspension, and the concentration of insecticide in said suspension are regulated such that the insecticide content of said impregnated granules is between about 0.1% and 0.5%, by weight.

7. A granular insecticide composition especially adapted for aerial distribution over flooded or flood-prone areas through a foliage canopy prepared by the steps of:
(a) providing a quantity of corncob granules having nominal diameters between about ¼ inch and ⅜ inch;
(b) providing a quantity of a suspension of an insecticide in a liquid suspending agent with which said insecticide has only limited miscibility;
(c) impregnating said corncob granules with said suspension while regulating the respective quantities of said corncob granules and said suspension, and the concentration of insecticide in said suspension to provide an effective amount of said insecticide on said impregnated granules whereby said suspending agent is absorbed into said corncob granules and an effective amount of said insecticide is deposited on the surface of said corncob granules.

8. The insecticide composition of claim 7 wherein said insecticide comprises a liquid organophosphate insecticide and said suspending agent comprises a liquid hydrocarbon, and said insecticide comprises between about 2% and 5%, by weight, of said suspension.

9. The insecticide composition of claim 8 wherein said liquid hydrocarbon is chosen from the group consisting of #1 diesel oil, #2 diesel oil, and petroleum naptha.

10. The insecticide composition of claim 7 wherein said suspension is applied to said corncob granules by spraying during agitation of said granules to effect substantially uniform impregnation of said granules with said suspension.

11. The insecticide composition of claim 7 wherein said corncob granules are prepared by grinding corn cobs.

12. The composition of claim 7 wherein said insecticide comprises between about 0.1% and 0.5%, by weight, of said impregnated granules.

13. A method of applying insecticide to the surface of a water insect breeding area which comprises the step of dispersing an effective amount of the granular insecticide composition of claim 7 over said surface.

14. A method of applying insecticide to the surface of a water insect breeding area which comprises the step of dispersing an effective amount of the granular insecticide composition of claim 8 over said surface.

15. A method of applying insecticide to the surface of a water insect breeding area which comprises the step of dispersing an effective amount of the granular insecticide composition of claim 9 over said surface.

16. A method of applying insecticide to the surface of a water insect breeding area which comprises the step of dispersing an effective amount of the granular insecticide composition of claim 10 over said surface.

17. A method of applying insecticide to the surface of a water insect breeding area which comprises the step of dispersing an effective amount of the granular insecticide composition of claim 11 over said surface.

18. A method of applying insecticide to the surface of a water insect breeding area which comprises the step of dispersing an effective amount of the granular insecticide composition of claim 12 over said surface.

* * * * *